Sept. 28, 1965 G. DE RUITER Plant Pat. 2,557
ROSE PLANT
Filed July 30, 1964
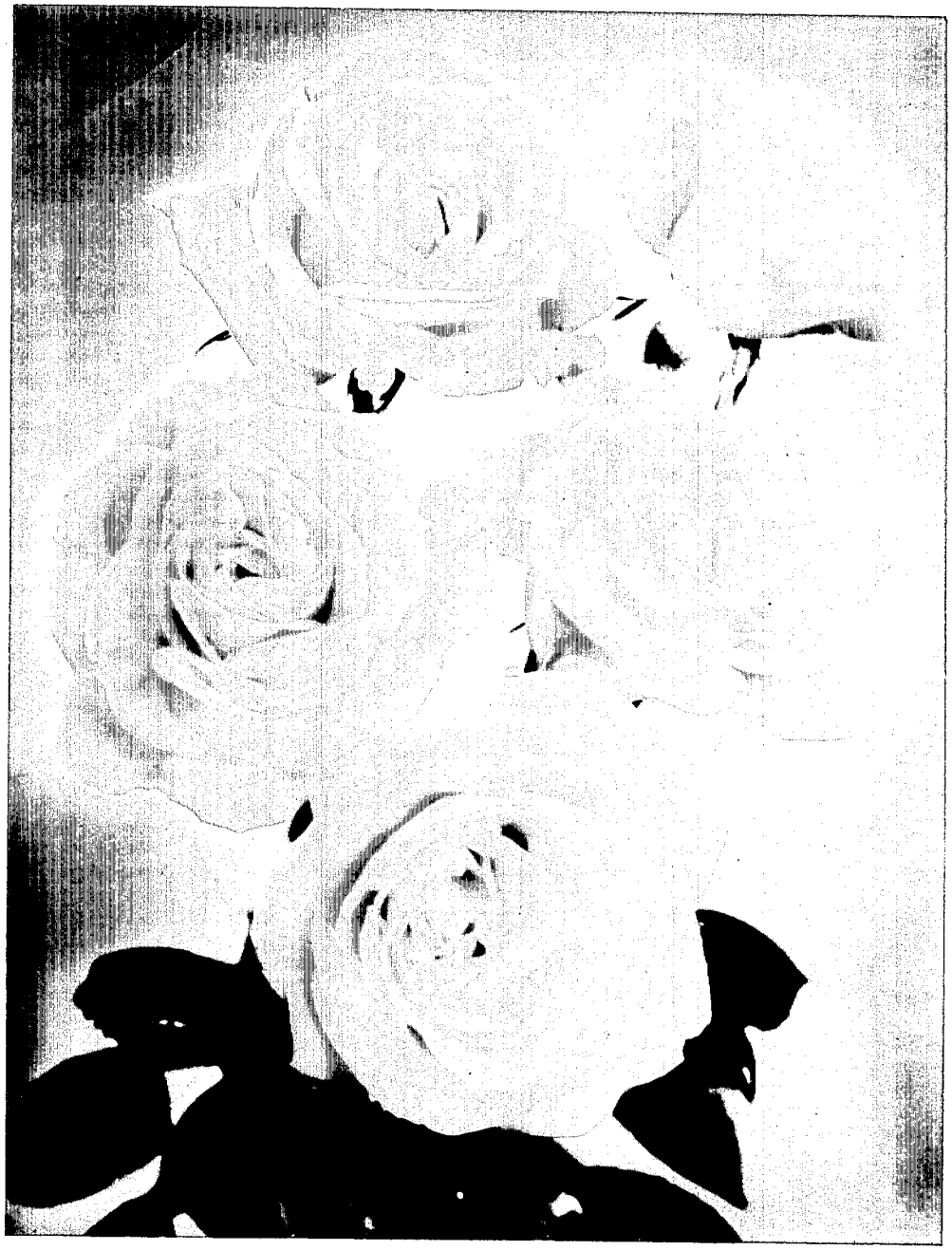
Inventor.
Gerrit de Ruiter
By: Robbs & Robbs
Attorneys.

United States Patent Office

Plant Pat. 2,557
Patented Sept. 28, 1965

2,557
ROSE PLANT

Gerrit de Ruiter, Hazerswoude, Netherlands, assignor to Carlton Rose Nurseries, Carlton, Oreg., a corporation of Oregon Filed July 30, 1964, Ser. No. 386,468
1 Claim. (Cl. Plt.—28)

The present invention relates to a new and distinct variety of rose plant of the floribunda class, which was originated by me by crossing the variety "Moulin Rouge" (U.S. Plant Patent No. 1,298) with the variety "Fr. Anny Beaufays" (unpatented).

As the result of this breeding, I have produced a new rose variety which is distinguished from its parents and from all other varieties of which I am aware, as evidenced by the following unique combination of characteristics which are outstanding therein:

(1) A vigorous habit of growth;

(2) Abundant, heavy, leathery, attractive, dark green, disease resistant foliage;

(3) A profuse blooming habit during both long summer days and short winter days;

(4) Strong flower stems of medium length;

(5) A distinctive, attractive and rich Dutch Vermilion flower color which is retained for prolonged periods both on the bush and as cut flowers;

(6) Long-lasting flower qualities and consequent persistence of the petals for extended periods without falling; and (7) A suitability for garden decoration and for commercial production of cut flowers of excellent quality.

Asexual reproduction of my new rose variety by both budding and grafting, as performed by me at Hazerswoude, Netherlands, shows that the foregoing characteristics and distinctions come true to form and are established and transmitted through succeeding propagations.

The accompanying drawing shows typical specimens of the flowers and foliage of my new variety, as depicted in color as nearly true as it is reasonably possible to make the same in a color illustration of this character.

The following is a detailed description of my new variety, with color terminology in accordance with the Horticultural Colour Chart, issued by the British Colour Council in collaboration with the Royal Horticultural Society, except where general color terms of ordinary dictionary significance are obvious:

Type: Hardy; bush; greenhouse and outdoor; seedling; for cut flowers and for garden decoration.

Class: Floribunda.

Breeding: Seedling.

*Seed parent.*—"Moulin Rouge."

*Pollen parent.*—"Fr. Anny Beaufays."

Propagation: Holds its distinguishing characteristics through succeeding propagations by both budding and grafting.

*Flower*

Locality where grown and observed: Hazerswoude, Netherlands, and Carlton, Oregon, U.S.A.

Flowers borne: Usually singly; strong; on long stems of medium length.

Quantity of bloom: Abundant, both outdoors and in greenhouse.

Continuity: Continuous.

Fragrance: Slight. Nature—centifolia.

Bud:

*Peduncle.*—Short; heavy; erect; stiff, entirely smooth; with few prickles. Color—medium green.

*Before calyx breaks.*—Size—medium. Form—oval; without a conspicuous neck; without foliaceous appendages on the surface of the bud; with foliaceous parts extending beyond the tip of the bud equal to ¼ of its length. Color—Dutch Vermilion, Plate 717/3.

*As calyx breaks.*—Color—Dutch Vermilion, Plate 717.

*As first petal opens.*—Size—large. Form—ovoid. Color:—outside—Dutch Vermilion, Plate 717/1; inside—Dutch Vermilion, Plate 717.

*Opening.*—Opens up well; is retarded by cold weather.

Bloom:

*Size (when fully open).*—From 3 inches to 3½ inches.

*Petalage.*—Very double; from 50 to 55 petals; arranged regularly.

*Form.*—Full centered and globular at first, but becoming high-centered; petals being at first tightly rolled outward and remaining tightly rolled outward at maturity, but usually with no stamens showing.

Petals:

*Texture.*—Thick; leathery.

*Appearance.*—Inside—velvety. Outside—velvety.

*Shape.*—Outer—oval, with apex flat. Intermediate—oval-ovate, with apex flat. Inner—oval-ovate, with apex flat.

This description of a newly opened flower was made from a rose grown in a greenhouse during the month of June at Carlton, Oregon, U.S.A.:

*Color.*—Outer petal: outside surface—Dutch Vermilion, Plate 717/1. Inside surface—Dutch Vermilion, Plate 717. Intermediate petal: outside surface—Dutch Vermilion, Plate 717/1; inside surface—Dutch Vermilion, Plate 717. Inner petal: outside surface—Dutch Vermilion, Plate 717/1; inside surface—Dutch Vermilion, Plate 717.

This description was made from a rose that was open for three days in a greenhouse during the month of June at Carlton, Oregon, U.S.A.:

*Color.*—Outer petal: outside surface—Dutch Vermilion, Plate 717/1; inside surface—Dutch Vermilion, Plate 717. Inner petal:—outside surface—Dutch Vermilion, Plate 717/1; inside surface—Dutch Vermilion, Plate 717.

*General color effect.*—Newly opened flower—a striking, solid Dutch Vermilion color. Three-days open—flowers hold the same color for a prolonged period of time, except for a small area of light gold color at the very base of the petals.

*Behavior.*—Persist; fading light orange; accelerated by heat.

*Flower longevity.*—On bush in garden—10 days in June. Cut roses grown outdoors and kept at living room temperatures—from 10 to 14 days in June. Cut roses grown in greenhouse and kept at living room temperatures—from 10 to 14 days in June.

*Reproductive organs*

Stamens: Many; arranged irregularly about pistils.

Filaments: Short; most with anthers. Color—yellow.

Anthers: Medium size; open at various times. Color—reddish brown.

Pollen: Moderate abundance. Color—gold.

Pistils: Many.

Styles: Uneven; short; heavy; bunched.

Stigma: Color—yellow.

Ovaries: All enclosed in calyx.

Hips: Ovoid; without a conspicuous neck; smooth; walls thick and fleshy. Color—reddish.

Sepals: Permanent; moderate length; spear-shaped. Color—Spinach Green, Plate 0960/3.

Seeds: Many; medium size.

*Plant*

Foliage:

*Leaves.*—Compound of 5 leaflets; abundant; large; heavy; leathery.

*Leaflets.*—Shape—ovoid, with apex acute. Base—round-obtuse. Margin—simply serrate.

*Color.*—Mature: upper surface—dark green, corresponding to Ivy Green, Plate 0001060/3; under surface—moderately dark green. Young: upper surface—moderately light red; under surface—moderately light red.

*Rachis (the supporting stem of the compound leaf).*—Heavy. Upper side—smooth. Underside—sparsely thorny.

*Stipules.*—Long; narrow; with long points turning out at an angle of less than 45°.

*Disease resistance.*—Excellent resistance to mildew and other fungi, as determined by comparison with other varieties grown under the same greenhouse and field conditions in both the Netherlands and Carlton, Oregon, U.S.A.

Growth:

*Habit.*—Bushy; upright; much-branched.

*Growth.*—Free; vigorous.

*Canes.*—Heavy.

*Main stems.*—Color—bright green. Thorns—few; medium length; hooked downward; with long, narrow base. Prickles—none. Hairs—none.

*Branches.*—Color—bright green. Thorns—few; medium length; hooked downward; with long, narrow base. Prickles—none. Hairs—none.

*New shoots.*—Color—bright red. Thorns—few; medium length; hooked downward; with long, narrow base. Prickles—none. Hairs—none.

I claim:

A new and distinct variety of rose plant of the floribunda class, substantially as herein shown and described, characterized particularly as to novelty by the unique combination of a vigorous habit of growth, abundant, heavy, leathery, attractive, dark green, disease resistant foliage, a profuse blooming habit during both long summer days and short winter days, strong flower stems of medium length; a distinctive, attractive and rich Dutch Vermilion flower color which is retained for prolonged periods both on the bush and as cut flowers, long-lasting flower qualities and consequent persistence of the petals for extended periods without falling, and a suitability for garden decoration and for commercial production of cut flowers of excellent quality.

No references cited.

ABRAHAM G. STONE, *Primary Examiner.*